(12) United States Patent
Knobel

(10) Patent No.: US 11,630,116 B2
(45) Date of Patent: Apr. 18, 2023

(54) TECHNIQUES FOR DETERMINING COAGULATION RESULTS

(71) Applicant: Roche Diagnostics Operations, Inc., Indianapolis, IN (US)

(72) Inventor: Rolf Knobel, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1329 days.

(21) Appl. No.: 16/023,591

(22) Filed: Jun. 29, 2018

(65) Prior Publication Data
US 2019/0018030 A1 Jan. 17, 2019

(30) Foreign Application Priority Data
Jul. 17, 2017 (EP) ..................................... 17181666

(51) Int. Cl.
*G01N 35/00* (2006.01)
*G01N 33/49* (2006.01)
(Continued)

(52) U.S. Cl.
CPC ... *G01N 35/00722* (2013.01); *G01N 33/4905* (2013.01); *G16H 10/40* (2018.01); *G16H 50/50* (2018.01); *G06F 2111/10* (2020.01)

(58) Field of Classification Search
CPC ......... G01N 35/00722; G01N 33/4905; G01N 33/48; G16H 10/40; G16H 50/50; G06F 2111/10
(Continued)

(56) References Cited

U.S. PATENT DOCUMENTS 6,524,861 B1 2/2003 Anderson
9,476,893 B2 10/2016 Mitsuyama et al.
(Continued)

FOREIGN PATENT DOCUMENTS

EP 0861687 A1 9/1998
EP 0932041 A2 7/1999
(Continued)

OTHER PUBLICATIONS

Fukushi, Ken, Blood clotting time tests using an automated coagulation analyzer, Journal of Analytical Bio-Science, 2009, pp. 408-416, vol. 32, No. 5.
(Continued)

*Primary Examiner* — Farhana A Hoque
(74) *Attorney, Agent, or Firm* — Taft Stettinius & Hollister LLP

(57) ABSTRACT

An automated method for determining a coagulation result of a biological sample is presented. The method includes obtaining a time series representing measurement data of a sample. The time series spans a period in which a clotting reaction is supposed to take place. The method includes obtaining a global model function configured to model measurement data of a sample in which a clotting reaction takes place. The global model function is configured to model the measurement data as a sigmoidal shape with at least one inflection point. The absolute value of the maximum curvature of the sigmoidal shape is larger on one side of the at least one inflection point than on the other side. The method includes fitting the model function to the time series representing measurement data to obtain a fitted model function and determining a coagulation result of the sample based on the fitted model function.

14 Claims, 6 Drawing Sheets

(51) Int. Cl.
*G16H 10/40* (2018.01)
*G16H 50/50* (2018.01)
*G06F 111/10* (2020.01)

(58) Field of Classification Search
USPC .......................................................... 703/11
See application file for complete search history.

(56) References Cited

U.S. PATENT DOCUMENTS

2012/0035450 A1    2/2012  Hayashi
2013/0122596 A1    5/2013  Kamihara et al.

FOREIGN PATENT DOCUMENTS

| EP | 1316802 A2 | 6/2003 | |
| EP | 1798652 B1 | 8/2010 | |
| EP | 2711713 A1 | 3/2014 | |
| WO | 2010/079845 A1 | 7/2010 | |
| WO | 2014/014484 A1 | 1/2014 | |
| WO | 2014/080751 A1 | 5/2014 | |
| WO | WO-2015000695 A1 * | 1/2015 | ............. G01N 21/49 |
| WO | WO-2016210424 A1 * | 12/2016 | ............... C12Q 1/56 |

OTHER PUBLICATIONS

Laffan, Michael A. and Manning, Richard A., Investigation of Haemostasis, Dacie and Lewis Practical Haematology E-Book, 2016, pp. 366-409, Ch. 18.
European Search Report dated Jan. 16, 2018, in Application No. EP 17181666.3, 2 pp.

* cited by examiner

TECHNIQUES FOR DETERMINING COAGULATION RESULTS

CROSS-REFERENCE TO RELATED APPLICATIONS

This application claims priority to EP 17181666.3, filed Jul. 17, 2017, which is hereby incorporated by reference.

BACKGROUND

The present disclosure generally relates to methods and systems for determining a coagulation result of a biological sample.

Coagulation diagnostics (also known as clotting diagnostics) plays an important role in the daily routine of today's medical practitioners. Frequently, coagulation diagnostics involves partly or fully automated processes performed by automated analyzers. Usually, a measurement is repeated over a predetermined period of time to monitor changes in properties of a sample caused by coagulation reactions. The resulting time series of measurement data can then be processed to gain insight in the coagulation process and, in turn, a health condition of an individual the sample has been drawn from. In particular, the automated analyzers might be configured to automatically determine one or more coagulation results (e.g., a coagulation time or a magnitude of a signal change) based on measurement data generated.

This process can be error-prone, as a variety of different confounding factors might occur and lead the automatic determination process astray. For example, a time series of measurement data can include signal jumps (e.g., caused by a movement of a sample vessel or air bubbles in the sample) or signal outliers. Furthermore, reactions different from a reaction to be monitored might take place in the sample and can influence a coagulation result. In addition, or alternatively, errors in sample or reagent handling or other errors can result in unexpected shapes of the time series of the measurement data. In any of these cases or other cases, an automated analyzer automatically performing a coagulation result determination algorithm might determine erroneous coagulation results. This can have serious consequences, as erroneous coagulation results can influence diagnostic and therapeutic decisions, or can require costly repetitions of coagulation diagnostics.

SUMMARY

According to the present disclosure, an automated method for determining a coagulation result of a biological sample is presented. The method can comprise obtaining a time series representing measurement data of a biological sample. The time series can span a period in which a clotting reaction is supposed to take place in the biological sample. The method can also comprise obtaining a global model function configured to model measurement data of a biological sample in which a clotting reaction takes place. The global model function can be configured to model the measurement data as a sigmoidal shape with at least one inflection point. The absolute value of the maximum curvature of the sigmoidal shape can be larger on one side of the at least one inflection point than on the other side. The method can also comprise fitting the model function to the time series representing measurement data to obtain a fitted global model function and determining a coagulation result of the biological sample based on the fitted global model function.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
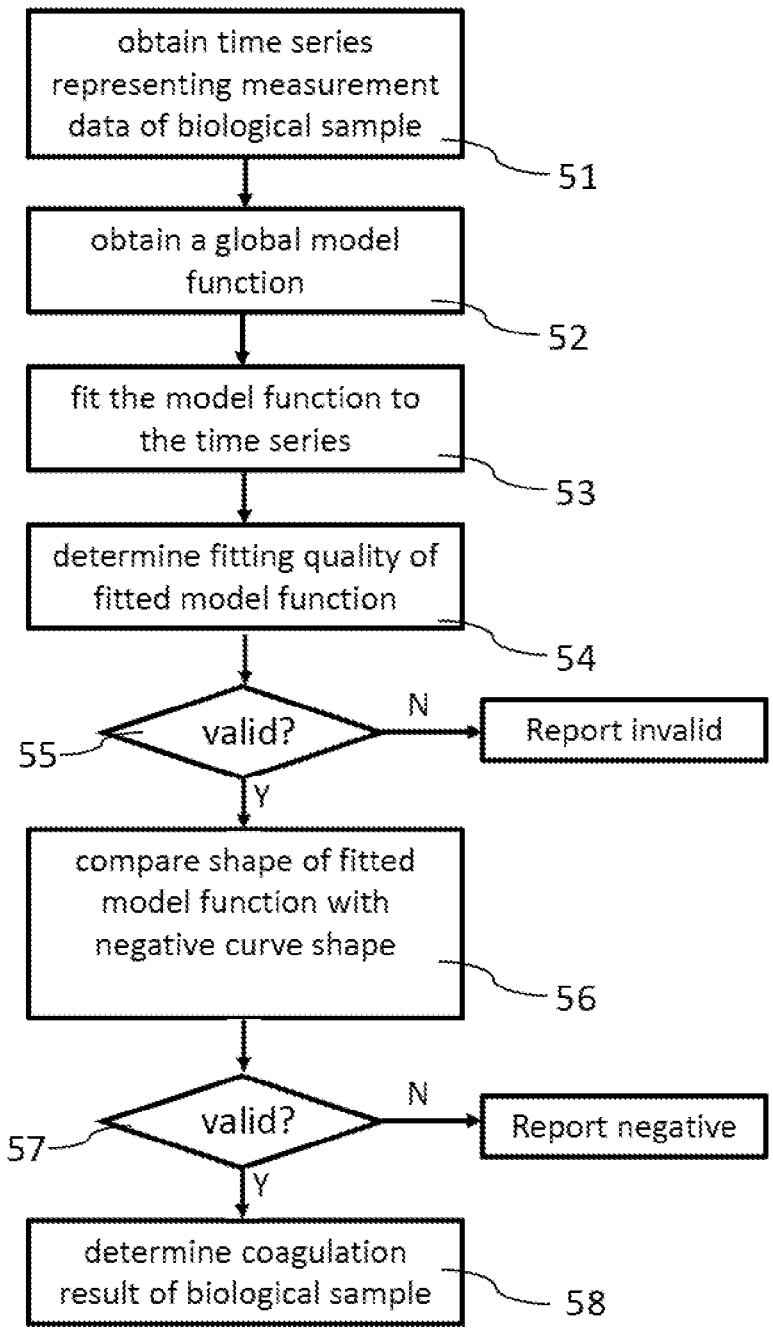
FIG. 1 illustrates a method for determining a coagulation result of a biological sample according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

An automated method for determining a coagulation result of a biological sample is presented. The method can include obtaining a time series representing measurement data of a biological sample. The time series can span a period in which a clotting reaction is supposed to take place in the biological sample. The method can also include obtaining a global model function configured to model measurement data of a biological sample in which a clotting reaction takes place. The global model function can be configured to model the measurement data as a sigmoidal shape with at least one inflection point. The absolute value of the maximum curvature of the sigmoidal shape can be larger on one side of the at least one inflection point than on the other side. The method can further include fitting the model function to the time series representing measurement data to obtain a fitted global model function and determining a coagulation result of the biological sample based on the fitted global model function.

A system for determining a coagulation result of a biological sample configured to carry out the steps of the above method of the present disclosure is also presented.

The above methods and the systems can have one of more of the following advantages in some embodiments.

In general, the techniques of the present disclosure can allow for a robust automated determination of coagulation results in some examples.

Firstly, by using a global model function, an influence of outliers or other erroneous data points can be diminished compared to some prior art techniques using a plurality of model functions to approximate the time series of measurement data piecewise. As a result, an outlier detection and removal process may not be required in some examples of the present disclosure.

Secondly, using a global model function can allow for a comparatively simple detection of signal jumps in a time series of measurement data. For example, a signal jump can result in a characteristic signature in a difference between fitted values and data values of a time series of measurement data which can be detected in a simple manner. Again, some prior art method which include piecewise fitting of different model functions may require more elaborate signal jump detection algorithms.

Thirdly, coagulation results can be automatically determined based on the fitted global model function being configured to model the measurement data as a sigmoidal shape according to the present disclosure in a simple and robust manner in some examples. In the case that the measurement data has a valid shape, the so defined global model function can be suitable to determine coagulation results for measurement data with a variety of differing characteristics. For example, different automated analyzers or assays used for coagulation diagnostics can yield quantitatively differing time series. In addition, different error sources and confounding factors can be present or absent in different environments. For instance, different interfering processes in a sample can lead to a drifting baseline or a tail in the measurement data for large time values in some situations.

When using the global model functions of the present disclosure, these errors and confounding factors can be automatically dealt with in some examples. Furthermore, the so defined global model functions can be tailored to a plurality of different environments (e.g., different analyzers or different assays used by a particular operator).

Fourthly, the global model function can be used to determine coagulation results even if there is no observed baseline in some examples. For instance, a measurement process may start delayed and/or a reagent triggering a coagulation reaction can be added prematurely. Some prior art techniques for automated coagulation result determination are not able to process such measurement data.

Fifthly, fitting a global model function according to the present disclosure can facilitate detection of invalid or negative (i.e., no clotting reaction has taken place) curve shapes in a relatively simple manner in some examples. For instance, one or more fitting quality parameters obtained in the process of fitting the global model function can be evaluated to determine that a time series of measurement data does not show a valid coagulation curve.

The term 'sigmoid' or 'sigmoidal shape' (the two terms are used interchangeably) as used herein can include all generally S-shaped curves. It can encompass but is not limited the special case of a logistic function as defined, e.g., by the formula $S(x)=1/(1+e^{-x})$.

A sigmoid or sigmoidal shape as defined herein can have at least one inflection point. However, in other examples, it can have more than one inflection point. The inflection point can be located at any position of the sigmoid (the sigmoid can have an asymmetric shape in which a signal growth or drop on one side of the inflection point is smaller than a respective signal growth or drop on the other side of the inflection point). A sigmoid or sigmoidal shape can be point symmetrical or asymmetrical about an inflection point.

A 'global model function' in the present disclosure can relate to a model function that can model a complete time series of coagulation data by fitting a single functional expression. In contrast to that, some prior art techniques using a plurality of local model functions to fit a time series piecewise.

The expression 'configured to model' can express a potential of a global model function to model a respective characteristic. Depending on the nature of a time series to which the model function is fitted, the fitted model may actually show the respective characteristic or not. For example, a model function being a sum of a linear and a non-linear term can be configured to model time series having a respective non-linear behavior. However, in the case where a sample time series is linear in time, the fitted model function can be linear as well (e.g., a weight of the non-linear term can be low or zero). In other words, even though a model function can be configured to model a certain characteristic, this may not mean that a fitted model function shows the respective characteristic in all instances.

Coagulation (also known as clotting) can be the process by which blood changes from a liquid to a gel, forming a blood clot. It can potentially result in hemostasis, the cessation of blood loss from a damaged vessel, followed by repair. The mechanism of coagulation can involve activation, adhesion, and aggregation of platelets along with deposition and maturation of fibrin. Disorders of coagulation can be disease states which can result in, e.g., hemorrhage or thrombosis. Coagulation mechanisms can be similar in all mammals and involve both a cellular (platelet) and a protein (coagulation factor) components. Coagulation can begin almost instantly after an injury to the blood vessel has damaged the endothelium lining the vessel. Leaking of blood through the endothelium can initiate two processes: changes in platelets, and the exposure of subendothelial tissue factor to plasma Factor VII, which can ultimately lead to fibrin formation. Platelets can immediately form a plug at the site of injury; this is called primary hemostasis. Secondary hemostasis can occur simultaneously. Additional coagulation factors or clotting factors beyond Factor VII can respond in a complex cascade to form fibrin strands, which strengthen the platelet plug.

The methods described herein can be used for any assay for coagulation diagnostics that is based on a time series of measurement data monitoring an ongoing coagulation reaction (e.g., as described above) in-vitro.

An 'automated analyzer' according to the present disclosure can be any automatic or semi-automatic device that is suitable to generate the measurement data processed by the techniques of the present disclosure. The automated analyzer can be equipped with any suitable measurement unit to carry out measurements that can be used to determine time series of measurement data for coagulation diagnostics.

For example, the automated analyzer can be configured to perform optical or electrical measurements on biological samples to generate the measurement data. The optical measurements can include one or more of a turbidity measurement, an absorbance measurement, a scattering measurement or a transmittance measurement. The electrical measurements can include and resistance measurement or an impedance measurement.

The term 'biological sample' can refer to material(s) that may potentially contain an analyte of interest for coagulation analysis. The sample can be derived from a biological source, such as a physiological fluid. In particular, the sample can be a whole blood sample or can be derived from a blood sample.

The biological sample can be pretreated prior to use, such as preparing plasma from blood. Methods of treatment can involve centrifugation, filtration, distillation, dilution, concentration and/or separation of sample components including analytes of interest, inactivation of interfering components, and the addition of reagents.

A sample may be used directly as obtained from the source or used following a pretreatment to modify the character of the sample. The biological sample can be a mixture of different materials. In particular, the biological sample can include non-biological materials, e.g., diluents, buffers or other additives that can be added prior to the coagulation analysis.

Unless specified otherwise, the term 'substantially' in the present disclosure can refer to a deviation of +/−10% from a predetermined value. For example, if the length of two elements is substantially equal, their actual lengths can differ by up to 10%. In the same manner, if an intensity distribution is substantially homogeneous, deviations from up to 10% from an average value might occur.

In connection with FIG. 1 and FIG. 2 different aspects of the methods and systems of the present disclosure will be discussed in general. Subsequently, in connection with FIG. 3, further aspects of determining a coagulation result will be covered in more detail. Particular choices of the global model function will be treated in more detail in connection with FIG. 4. Last, in connection with FIGS. 5*a-b* and FIGS. 6*a-b* example time series of measurement data that can be evaluated with the techniques of the present disclosure will be discussed.

Overview Over Techniques of the Present Disclosure

FIG. 1 illustrates an example method for determining a coagulation result of a biological sample according to the present disclosure.

The method can include the steps of obtaining a time series representing measurement data of a biological sample 51, obtaining a global model function configured to model measurement data of a biological sample 52, fitting the model function to the time series representing measurement data to obtain a fitted model function 53 and determining a coagulation result of the biological sample based on the fitted model function 58. These steps will be discussed in more detail in the subsequent section. The method can also include optional steps of validation of the fitted model function 54-57. These steps will be discussed in a separate section below.

Obtaining a time series representing measurement data of a biological sample 51 can include any automatically triggered or user triggered receipt of a time series representing measurement data (e.g., measurement data obtained by an automated analyzer). In one example, the processing steps can take place in a processing system of an automated analyzer performing the measurement operations yielding the time series (e.g., the measurement data can be obtained from a local memory). In other examples, the processing can take place on a processing system separate and/or remote from an automated analyzer performing the measurement operations yielding the time series. In these examples, the measurement data can be received through a network connection.

In any case, the time series can span a period in which a clotting reaction is supposed to take place in the biological sample. The period can be a preset period of the automated analyzer performing the measurement or a variable period that can be dynamically set by the automated analyzer performing the measurement.

In many cases, the automated analyzer can be configured to add a reagent to the biological sample to trigger a clotting reaction. In these examples, the time series can span a time starting shortly (e.g., about 0.1 s or more) after a reagent has been added. An end time of the period can be set after an expected point in time where the clotting reaction has substantially terminated. This point in time can also be referred to as 'saturation' in the present disclosure. It can be pointed out that it may not be possible to determine a concrete point in time as an end of the clotting reaction. However, the 'end of the clotting reaction' can be seen as a point in time where a predetermined major percentage of material in the sample has reacted (e.g., about 90% or more of the material). Some clotting reaction can (and most likely will) continue after this point in time.

Obtaining the global model function 52 can include retrieving a model function that can be stored in a memory of a processing system that carries out the methods for determining a coagulation result of a biological sample of the present disclosure. For example, the global model function can be contained in a control software of an automated analyzer.

The global model function can be adapted to model measurement data of a biological sample in which a clotting reaction takes place. The attribute 'global' can indicate that the model function can be adapted to model the entire time series starting at a point in time before the clotting reaction has started and ending after the slotting reaction has saturated (i.e., a change of the measurement data due to ongoing clotting reactions falls below a predetermined threshold). Further features of the global model functions of the present disclosure will be discussed below in connection with FIG. 2 and FIG. 4.

The step of fitting the model function to the time series representing measurement data to obtain a fitted model function 53 can include any suitable numerical technique to fit the model functions discussed in the present disclosure to a time series of measurement data. For example, the fitting process can include performing an (iterative) nonlinear regression using suitable numerical regression techniques. These techniques can include automatically generating starting values for fitting parameters of the global model function and iteratively optimizing these automatically generated starting values. The skilled person knows the available techniques and how they can be implemented to automatically perform the fitting operations of the present disclosure. Therefore, details regarding the implementation of the fitting step will not be discussed in more detail in the present disclosure.

The fitting process can take place locally on an automated analyzer performing the measurement of the biological sample. In other examples, the fitting process can be performed at a remote site. In one example, software providing the fitting capabilities can be stored at a remote server or in a cloud storage location and can be accessed remotely from a site where the automated analyzer is located.

The determination of a coagulation result of the biological sample based on the fitted model function can include determining one or more of a coagulation (or clotting) time or a magnitude of a signal change caused by a coagulation reaction determined based on the fitted global model function.

The coagulation time can be indicative of a time required for a biological sample to coagulate in-vitro under predetermined conditions. This value can be indicative of different health conditions. The magnitude of the signal change caused by a coagulation reaction can yield quantitative information regarding the ongoing coagulation reaction which can also be indicative of different health conditions.

Even though coagulation times and magnitudes of a signal changes will be discussed as example coagulation results in many passages of the present disclosure, the fitted model function can also be used to determine other features as coagulation results. Further details regarding the determination of the coagulation results will be discussed in connection with FIG. 3 below.

After an overview over the methods for determining a coagulation result of a biological sample according to the present disclosure has been given in the preceding section, the particular global model function employed in the techniques of the present disclosure will be discussed next.

The Global Model Function

Figure 2:
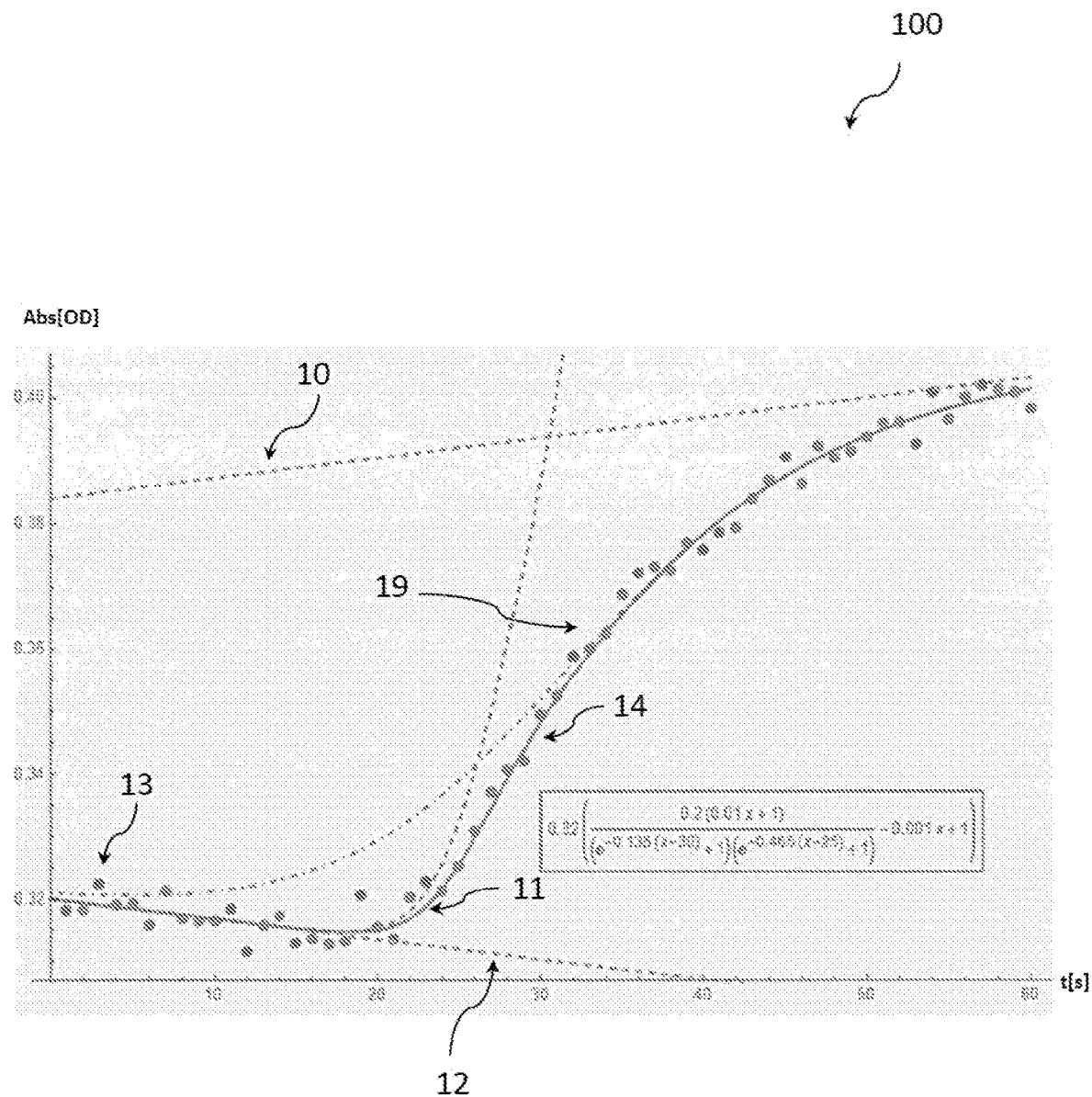
FIG. 2 illustrates an example plot of a time series of measurement data and a fitted model function according to an embodiment of the present disclosure.

FIG. 2 shows an example plot 100 of time series of measurement data and a fitted model function according to the present disclosure. In the example of FIG. 2 (and the subsequent examples), the time series of measurement data can include extinction (or optical density) values of the biological sample over time. The optical density of a biological sample can be proportional to a concentration of a target analyte in some examples.

In other examples, the time series can include data values for another parameter than extinction (or optical density) over time. For instance, the parameter can be a transmission or impedance of a biological sample (or include data values derived from these parameters). However, the techniques of the present disclosure can be equally applied in these cases where the measurement data traces another parameter than extinction (or optical density). In particular, the curve shapes of the measurement data can have similar characteristics for these parameters. Therefore, it can be possible to employ the global fitting models described in the present disclosure if the time series includes other measurement data than extinction data.

In the example of FIG. 2, the time series 13 cab represent a valid set of measurement data. In other words, a coagulation reaction has taken place in the biological sample as expected and no evident measurement errors have occurred.

It can be seen that the fitted model function 11 reflects the properties of the time series 13. In particular, the fitted model function 11 models the measurement data as a sigmoidal shape 19 with at least one inflection point 14. The absolute value of the maximum of curvature of the sigmoidal shape 19 is larger on one side (the left-hand side) of the at least one inflection point 14 than on the other side (the right-hand side). In other words, the fitted model function 11 can be point-asymmetric around the inflection point 14. Thus, the fitted model function 11 can exhibit a faster signal change (e.g., growth) in an earlier period of time up to a point in time of the inflection point 14 and a slower signal change (e.g., growth) in a later period of time starting at the point in time of the inflection point 14. The curve has a steeper onset and then transitions to a shallower portion. The relationship of the two sides may be reversed in other examples.

A relative position of the inflection point 14 can vary. For example, the inflection point 14 can be located in an early stage of the sigmoidal shape 19 (e.g., before the sigmoidal shape has reached 20% of its amplitude) or in a late stage of the sigmoidal shape 19 (e.g., after the sigmoidal shape has reached 80% of its amplitude).

In other cases, a difference in the absolute value of a maximum of curvature of the sigmoidal shape can be larger or smaller than depicted in FIG. 2. As will be discussed below, the global model function can be configured to model different differences in the absolute value of the maximum of curvature of the sigmoidal shape.

In some prior art examples of model functions for modeling measurement data in coagulation analysis, a fitted curve can have a symmetric shape about an inflection point. The model function of the present disclosure can be more flexibly adapted to different signal shapes one might encounter under different circumstances than the model functions of these examples.

In addition to the particular sigmoidal shape discussed above, the global model functions of the present disclosure can be configured to model one or more additional features of a time series of measurement data.

For example, the global model function can be configured to model a non-flat baseline of the sigmoidal shape. In other words, the baseline of the sigmoidal shape can change in time. In contrast to that, a logistic function has a flat baseline (i.e., for very small values of time ("on the left-hand side") the function value of the logistic function is substantially constant). The term 'baseline' can be used in the present disclosure as referring to a portion of a time series of measurement data/a fitted model function prior to a noticeable non-linear signal change caused by a clotting reaction to be observed (i.e., a "middle" portion of the sigmoidal shape).

As discussed above, a clotting reaction may not have yet started in this portion, or an effect of an ongoing clotting reaction may not yet be noticeable in the measurement data. The fitted function 11 in FIG. 2 models such a non-flat baseline 12. As can be seen, the baseline 12 falls linearly in a portion of the time series prior to a portion of the curve exhibiting a non-linear behavior.

In other examples, the baseline of the fitted model function can rise linearly. The global model function of the present disclosure can be configured to model rising, falling and flat baselines, or a selection of one or more of these (e.g., a particular model function can be provided to assume only a falling or only a rising baseline). In other examples, the model function can be configured to model a baseline that rises or falls in a non-linear manner.

The above described rise or fall of the baseline can be caused by reactions that take place in the biological sample other than a clotting reaction to be monitored in some examples.

In addition, or alternatively to a non-linear baseline, the global model function can be configured to model a non-flat virtual or actual asymptotic line 10 of the sigmoidal shape. The asymptotic line 10 can be thought as marking a signal level when no further change of a signal value due to a clotting reaction to be observed takes place.

Figure 5A:
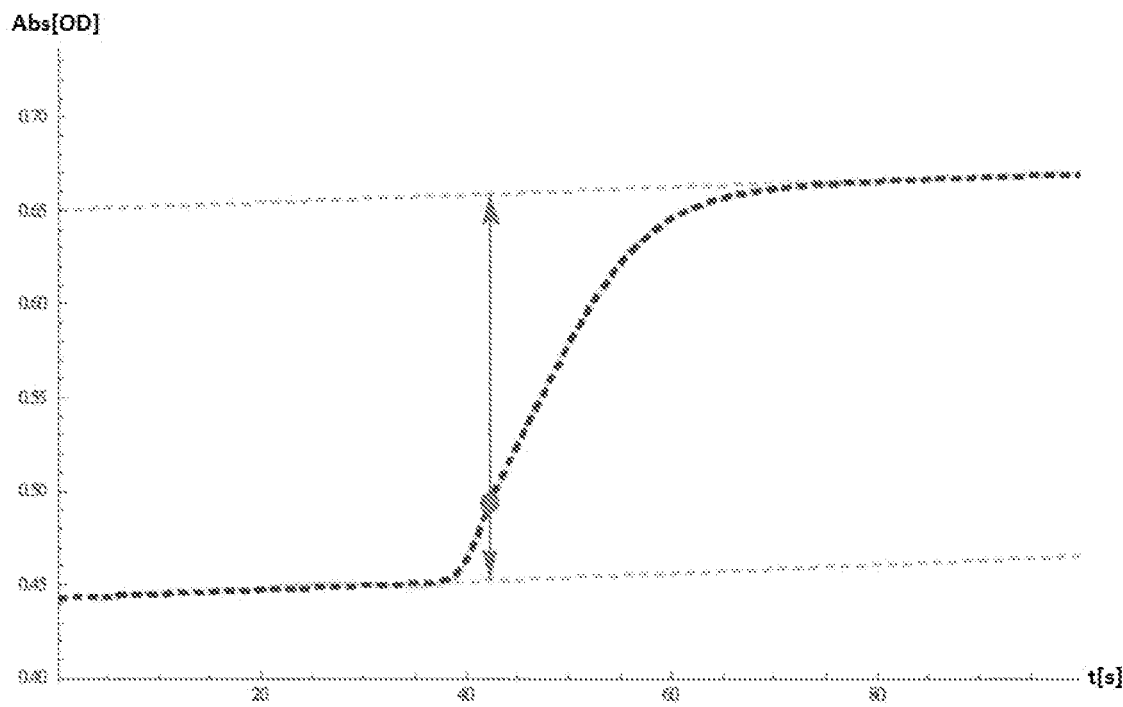
FIGS. 5a-b illustrate example time series of coagulation measurement data and fitted model functions according to an embodiment of the present disclosure.
Figure 5B:
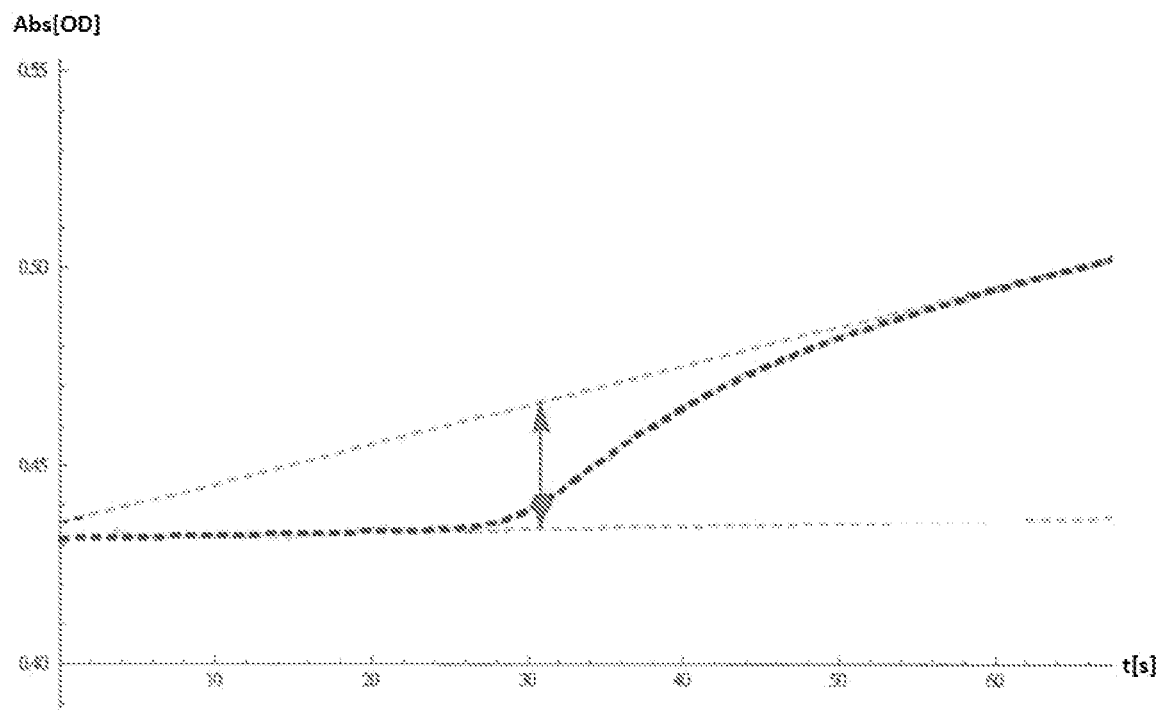
Figure 6A:
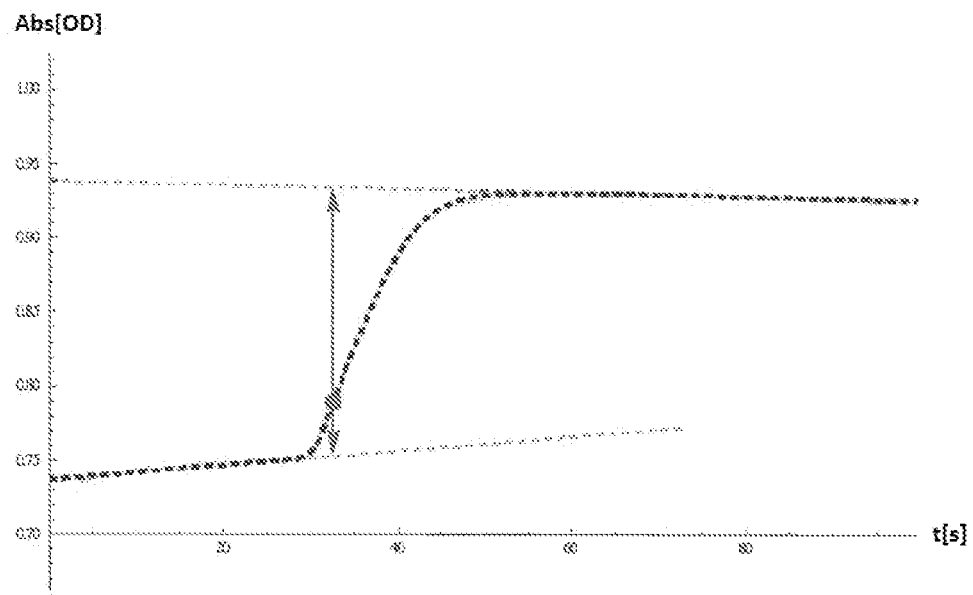
FIGS. 6a-b illustrate further example time series of coagulation measurement data and fitted model functions according to an embodiment of the present disclosure.

The asymptotic line can be an actual asymptotic line discernible in the fitted model function/the time series. In these cases, the fitted model function/the time series approaches the actual asymptotic line. Examples for fitted model functions having an actual asymptotic line are depicted in FIGS. 5a-b and FIG. 6a.

Figure 3:
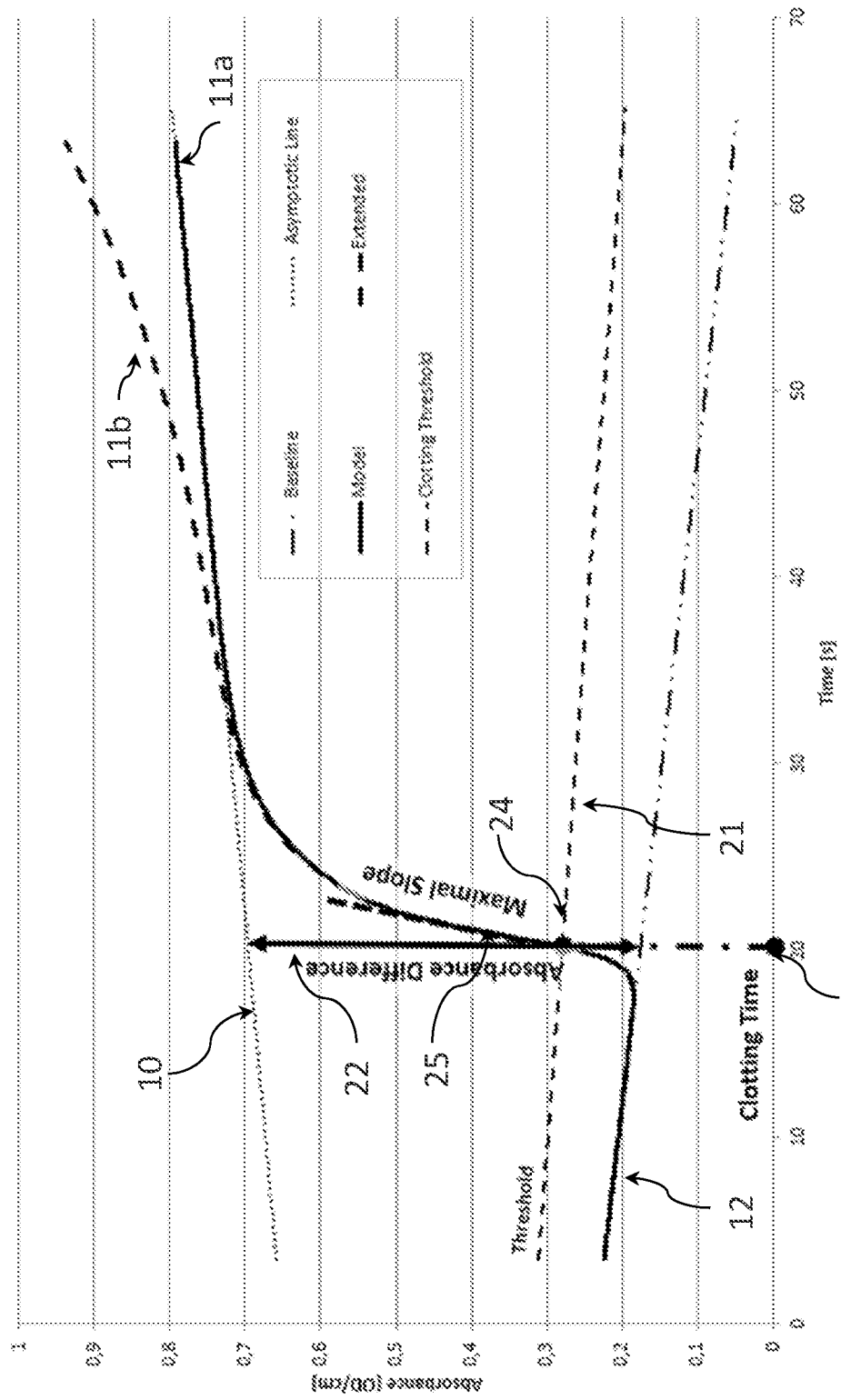
FIG. 3 illustrates an example process of determining coagulation results according to an embodiment of the present disclosure.

In other examples, the asymptotic line can be a virtual asymptotic line of the fitted model function/the time series. An example for this case is depicted in FIG. 3. As can be seen, the graph showing a fitted curve for an "extended model" has a tail with positive curvature. In other words, the fitted model function may not approach a linear asymptotic function but rather curves on the right hand side of the sigmoid shape. As discussed above, this tail can be the result of interfering processes in the biological sample that superpose a clotting reaction to be observed in the biological sample. For instance, a biological sample can be contaminated with hemolyzate (e.g., if a practitioner made a mistake when drawing a blood sample).

In these cases, the global model function of the present disclosure nevertheless can model a non-flat asymptotic curve. However, this asymptotic curve is not visible in the time series and the fitted model function due to the superposing processes. The virtual asymptotic line is an asymptotic line the time series/fitted model function would approach in the absence of interfering processes. For example, the virtual asymptotic line can be an asymptotic line the time series/fitted model function would approach in the absence of a tail with negative or positive curvature of the sigmoidal shape.

The fitted function 11 of FIG. 2 models a non-flat actual asymptotic line 10 in the time series of measurement data 13. As can be seen in FIG. 2, the fitted model function 11 and the time series of measurement data asymptotically approach the asymptotic line 10 (examples of virtual asymptotic lines will be discussed below in connection with FIG. 3 and FIG. 4). The discussion of the actual asymptotic line 10 of FIG. 2 in the following sections is equally applicable to cases where the fitted global model function defines virtual asymptotic lines.

In the example of FIG. 2, the asymptotic line 10 is a linearly rising line. In other examples, the asymptotic line 10 of the fitted model function can fall linearly. The global model function of the present disclosure can be adapted to model rising, falling and stationary asymptotic lines, or a selection of one or more of these (e.g., a particular model function can be provided to assume only a falling or only a rising asymptotic line). In other examples, the model function can be adapted to model an asymptotic line that rises or falls in a non-linear manner.

Having a capability to model non-flat baselines and/or asymptotic lines in a global model function for modeling measurement data of coagulation measurements can result in more accurate and robust determination of coagulation results in some examples.

Figure 4:
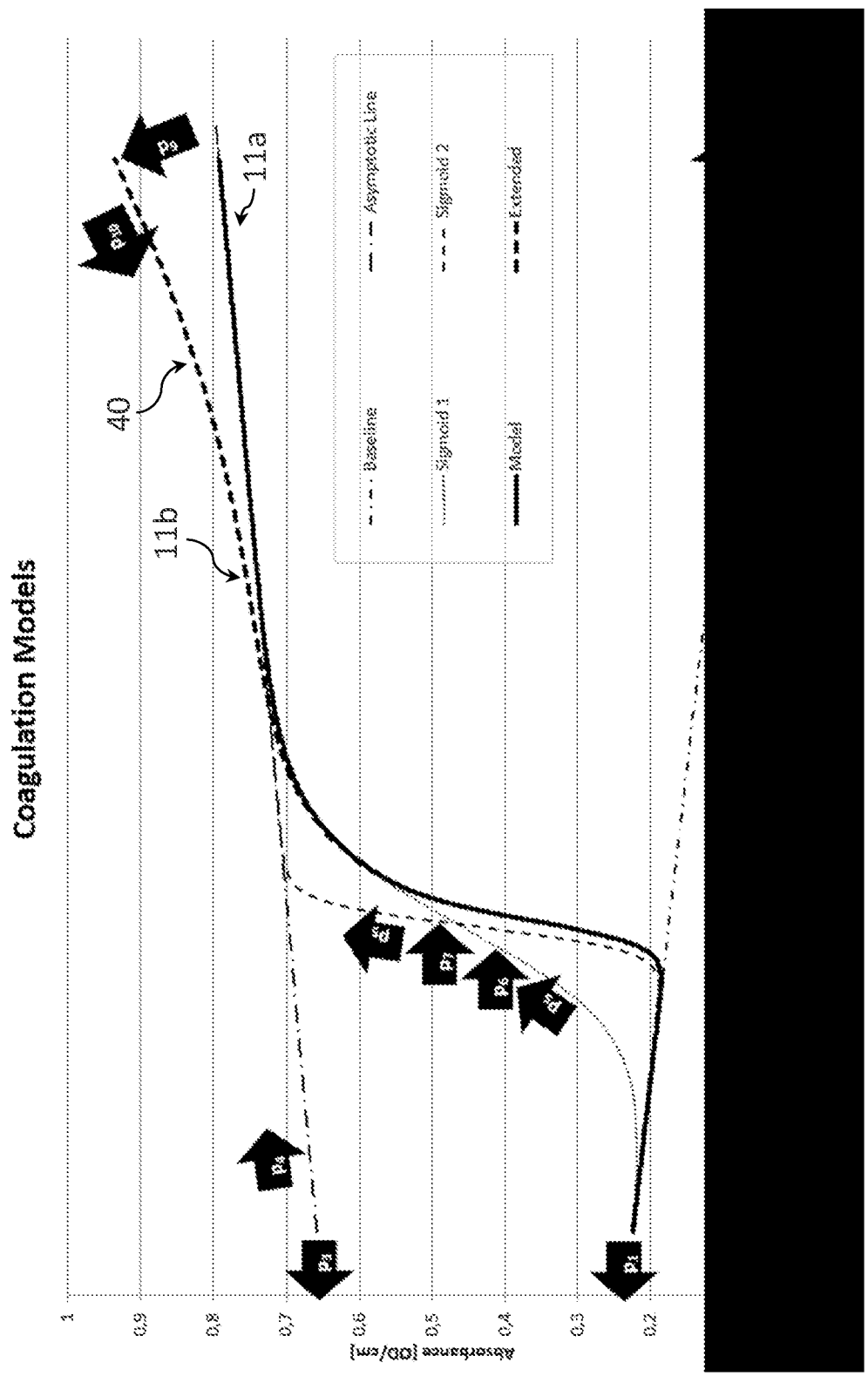
FIG. 4 illustrates how different fitting parameters of an example global model function influence an example fitted model function according to an embodiment of the present disclosure.

Further potential aspects of the global model functions of the present disclosure and particular example global model function will be discussed below in connection with FIG. 4. First, additional details of the determination process of the coagulation results will be treated.

Coagulation Result Determination

FIG. 3 illustrates an example process of determining coagulation results according to the present disclosure. As discussed above, a global model function has been fitted to a time series of measurement data to obtain a fitted model function. In the example of FIG. 3, two different fitted model functions 11a, 11b are shown being the result of using (slightly) different global model functions. Either of these fitted model functions 11a, 11b can subsequently be used to determine one or more coagulation results.

In one example, the determination process can include determining a baseline 12 based on the fitted model function, determining an actual or virtual asymptotic line 10 based on the fitted model function and defining a threshold line 21 running between the baseline and the asymptotic line.

As discussed above, the baseline 12 and/or the asymptotic line 10 can be non-flat (e.g., linearly rising or falling). The two fitted model functions 11a, 11b plotted in FIG. 3 differ in this respect. While the non-flat baseline 12 is the same for both fitted model functions, 11a, 11b, the (simple) global model leading to fitted model function 11a models a time series having an actual asymptotic line. The "extended model" of the global model function is configured to model a curved tail of the time series and leads to the fitted model function 11b. This fitted model function 11b/time series has a virtual asymptotic line, as discussed above. The techniques for determining the coagulation result can use either an actual or a virtual asymptotic line. Therefore, no distinction between the two case is made in the following section.

A distance between the baseline 12 and the threshold line 21 can be a fixed fraction of a distance between the baseline 12 and the asymptotic line 10 at each point in time. As both the baseline 12 and the asymptotic line 10 are linear in the example of FIG. 2, the threshold line 21 is also linear.

The fixed fraction can be set, e.g., depending on the type of test carried out on the biological sample or the type of automated analyzer generating the measurement results. In some examples, the fraction lies between about 0.05 and about 0.9 (e.g., set to a value between about 0.1 and about 0.6).

In a further step, determining a coagulation result can take place based on a feature of the fitted model function 11a, 11b where the fitted model function 11a, 11b crosses the threshold line 21. In the example of FIG. 2, the threshold line 21 crosses the fitted model function at a point 24.

In one example, a time value 23 corresponding to this point 24 can be determined as coagulation result. In this example, the coagulation result is a coagulation time (or clotting time).

In addition, or alternatively, a difference 22 (or a fraction thereof) between the baseline 12 and the asymptotic line 10 at the point in time 23 where the fitted model function 11a, 11b crosses the threshold line 21 can be determined as coagulation result. In this example, the coagulation result quantifies a magnitude of a signal change of the measurement data caused by the clotting reaction.

In other examples, a coagulation time or magnitude of a signal change of the measurement data caused by an ongoing clotting reaction can be determined in other ways than the ways discussed above.

For instance, determining a coagulation result can include either determining a baseline based on the fitted model function or determining an asymptotic line based on the fitted model function. In a further step, the method can comprise defining a threshold line as either a fixed multiple of the baseline value or a fixed fraction of the asymptotic line at each point in time. Determining the coagulation result can happen based on one or more parameters of the fitted model function where the fitted model function crosses the threshold line. The coagulation result can be a coagulation time or magnitude of a signal of the measurement data caused by an ongoing clotting reaction, as discussed above.

In still other examples, the coagulation time can be determined as a time of a point of maximum slope 25 of the fitted model function or another salient feature of the fitted model function.

In still other examples (and in addition to the coagulation results above), determining a coagulation result can include determining other features of the fitted model function or determining other values of the fitted model function.

For example, a signal level at an axis intercept of the baseline, the asymptotic line, or both can be used to determine a coagulation result. In other example, a signal level at a predetermined other point in time of the baseline, the asymptotic line, or both can be used to determine a coagulation result. However, in some examples, an absolute value of a level of the baseline and the asymptotic line alone carries no information that is relevant for determining a coagulation result (in contrast to a difference between the levels of the baseline and the asymptotic line).

As discussed above, the baseline of the fitted model function, the asymptotic line of the fitted model function, or both can be used in the process of determining the coagulation result. In some examples, the baseline, the asymptotic line, or both can be determined using one or more subset of fitting parameters of the fitted model function. Further details regarding this process will be discussed below.

In the examples of the detailed description, the signal change in the fitted model function is depicted as positive (e.g., increasing from a lower level baseline). However, depending on the measurement technique employed to generate the time series and/or the representation of the measurement data, the signal change can also be negative (e.g., dropping from a higher level baseline). For instance, the graph in FIG. 3 depicts a measured absorbance and shows that the absorbance of the biological sample increases as time progresses. However, in other examples a transmittance of a biological sample can be detected which might decrease for the same sample as time progresses. The techniques of the present disclosure can be applied likewise in any of these situations.

Example Global Model Functions

After having discussed general properties the global model function the present disclosure can have above, different example global model functions will be discussed subsequently in connection with FIG. 4.

The graph in FIG. 4 again shows two example fitted model functions 11a, 11b generated by using two different global model functions (a "simple" model and an "extended" model) of the present disclosure and illustrates how different fitting parameters can influence the fitted model function.

As can be seen, the fitted model functions define a non-stationary baseline, a non-stationary asymptotic line (an actual asymptotic line in the case of fitted model function 11a and a virtual asymptotic line in the case of fitted model function 11b) and models the time series as an asymmetric sigmoidal shape, as discussed above.

In addition, the model function can be configured to model a non-linear tail 40 with a positive curvature of the measurement data. The fitted model function 11b shows this property. In other words, the measurement data does not increase or decrease linearly or remain constant in a period of time following a nonlinear portion of the sigmoidal shape. In other examples, a tail of the measurement data can have a negative curvature.

In some examples, the global model function of the present disclosure can include a sum of three or four terms. The terms can be adapted to model different features of a time series of measurement data.

For instance, a first term is a constant term defining a baseline intercept, a second term can be a linear term defining a baseline slope, and a third term can be a non-linear term modeling a signal change after a clotting reaction to be monitored has started (i.e., defining a non-linear behavior of the sigmoidal shape).

The third term can be a product of a linear component and two or more exponential components. For example, the linear component can define a (virtual or actual) asymptotic line and the two or more exponential components can define a shape of a non-linear portion of the sigmoidal shape.

In addition, a fourth term can be a non-linear term defining a non-linear behavior in a tail of the model function (e.g., a positive or negative curvature of the tail of the model function).

A first example of a global model function can be represented as follows:

$$f_m(x, \vec{p}) = p_1\left(1 + p_2 \cdot x + \frac{p_3(1 + p_4 \cdot x)}{(1 + e^{-p_5(x-p_6)}) \cdot (1 + e^{-p_7(x-p_8)})}\right). \quad \text{(equation 1)}$$

In this representation, the terms $p_i$ represent fitting parameters (with the index i running from 1 to 8) and x denotes a time value of the time series to be fitted. Fitting the model function to a time series can include finding a set of fitting parameters $p_i$ leading to a fitted model function which matches the time series as closely as possible (e.g., minimizing a quality criterion such as a least square criterion). As discussed above, nonlinear regression techniques can be employed to solve this problem.

The global model function of equation 1 is adapted to model an asymmetric sigmoidal shape as well as a non-flat baseline and a non-flat actual asymptotic line (i.e., the sigmoidal shape approaches the asymptotic line). In this example, the baseline and the asymptotic line are modeled linearly. In other words, the fitted model function approaches linear functions left and right of the sigmoidal shape. As can be seen, a slope of the linear baseline and the linear asymptotic line can be different.

The influence of the different fitting parameters on the shape of the fitted model function will be discussed next. This is also indicated in FIG. 4 which depicts arrows including the respective fitting parameter to highlight is respective influence.

A first fitting parameter $p_1$ defines a baseline intercept. As can be seen, for a time x=0 the influence of all parameters expect for $p_1$ is small. The exponential terms suppress the influence of the last term for small values of x. Moreover, a second fitting parameter $p_2$ defines a baseline slope together with the first fitting parameter $p_1$. Therefore, the baseline is defined by the term $p_1(1+p_2 x)$.

A third fitting parameter $p_3$ influences a difference of an intercept of the (virtual or actual) asymptotic line to an intercept of the base line. A fourth fitting parameter $p_4$ influences a slope of the (virtual or actual) asymptotic line. As can be seen in equation 1, the numerator of the third term including the exponential factors also defines a linear relationship ($p_3(1+p_4 x)$). Thus, for time x=0 the equation assumes the value $p_1+p_1p_3$. Furthermore, for large time values the exponential terms are close to 1. This means that the equation approximately has the value:

$$f(\text{large } x) = p_1(1+p_2x+p_3(1+p_4x)).$$

It can be seen that this again is a linear function which can be offset compared to the baseline and have a different slope due to the effect of the term $p_3(1+p_4 x)$. In other words, a subset of fitting parameters (e.g., $p_1$ to $p_4$) defines the shape of the baseline and the asymptotic line. Therefore, these fitting parameters can be used in the process of determining the coagulation results involving the baseline and the asymptotic line discussed above.

Returning to equation 1, the parameters in the denominator of the third term of equation 1 define a shape and position of a non-linear portion of the fitted model function which models an influence of a clotting reaction to be observed. In the example of equation 1, the model function includes a product of two logistic functions (i.e., symmetric sigmoids) which can have different shapes and different positions in time of a respective inflection point. As a result, their product can define an asymmetric sigmoidal shape, as discussed above.

The logistic functions approach the value zero for small (time) values x and the value 1 for large values of x. As a consequence, the logistic functions only influence the shape of the fitted model function in a certain period of time. The remaining terms determine a shape of the sigmoidal shape for earlier and later times.

In the example of equation 1, a fifth fitting parameter $p_5$ defines a steepness of a first sigmoid modeling the non-linear portion of the fitted model function which models an influence of a clotting reaction to be observed and a sixth fitting parameter $p_6$ defines a position in time of an inflection point of a first sigmoid modeling the non-linear portion of the fitted model function which models an influence of a clotting reaction to be observed. Accordingly, a seventh fitting parameter $p_7$ defines a steepness of a second sigmoid modeling the non-linear portion of the fitted model function which models an influence of a clotting reaction to be observed and an eighth fitting $p_8$ parameter defines a position in time of an inflection point of a second sigmoid modeling the signal non-linear portion of the fitted model function which models an influence of a clotting reaction to be observed (as can be seen in equation 1, the linear terms can also influence the non-linear portion in some examples).

It becomes clear from equation 1 that the fitted model function is influenced by the sigmoids of the third term over its complete extension. Therefore, even for early times the fitted model function might not be strictly linear in time. However, a deviation from a linear behavior is not noticeable in this period of time and the baseline is thus considered to be linear.

Even though the global model function has a particular form in equation 1, this form can vary in other examples. For example, the model function of equation 1 can transformed into a mathematically equivalent formulation (i.e., by applying operations which change the representation of the formula). For example, an equivalent formulation can include solving the outer brackets of equation 1. In this example, the fitting parameter might be different. The equivalent model function can also be used to fit a time series of measurement data as discussed in the present disclosure.

Moreover, in other examples the model function can be modified in different ways. For instance, a third (or third and fourth) logistic function(s) could be added in the product of the last term. In addition, or alternatively, the linear terms in equation 1 can be replaced by non-linear terms. Further variations will be discussed below.

The global model function of equation 1 (or its mathematical equivalents) can be suitable to fit a wide variety of shapes of time series that occur in coagulation diagnostics without using an overly large set of parameters. As a result, the fitted model functions can be accurate (e.g., relevant features can be reflected) and at the same time robust and comparatively simple to calculate (due to a comparatively low number of fitting parameters). In examples of other model functions, either the accuracy might be lower due to simpler models (e.g., having a point-symmetric sigmoidal shape or stationary baselines) or the robustness might be lower due to a larger number of fitting parameters.

A second example of a global model function can be represented as follows:

$$f_m(x, \vec{p}) = p_1 \left(1 + p_2 \cdot x + \frac{p_3(1 + p_4 \cdot x)}{(1 + e^{-p_5(x-p_6)}) \cdot (1 + e^{-p_7(x-p_8)})} + \frac{p_9}{(1 + e^{-p_{10}(x-x_{max})})}\right), \quad \text{(equation 2)}$$

Here, the terms $p_i$ again represent fitting parameters (with the index i running from 1 to 10) and x denotes a time value of the time series to be fitted and $x_{MAX}$ can be another fitting parameter or a fixed value. As can be seen, the first three terms are identical to the respective terms of equation 1. The discussion above regarding these parameters likewise applies to equation 2.

In addition, equation 2 includes a fourth term being a non-linear term defining a non-linear behavior in a tail of the model function. The term includes another logistic function. This means that the fourth term does not influence the shape of the fitted model function for small values of x (i.e., for early times).

In detail, the fourth term includes a ninth and a tenth fitting parameter ($p_9$, $p_{10}$). The value $x_{MAX}$ can be defined as the maximal time of the time series measurement (thus, $x_{MAX}$ is a fixed value in the fitting process). In other examples, the value $x_{MAX}$ can be defined as another fixed value determined based on the time series or otherwise. The tenth fitting parameter $p_{10}$ influences a curvature of the tail of the model function and the ninth fitting parameter $p_9$ models an amplitude of a non-linear change of a tail of the measurement data.

In other examples, one or more terms modeling a non-linear behavior in a tail of the model function can include different functions than a logistic function.

After several example global model functions have been explained in more detail, further modifications and application examples will be discussed subsequently in connection with FIGS. 5a-b and FIGS. 6a-b.

Application Examples and Further Variations

The model functions of the present disclosure can be suitable to model a large variety of curve shapes of measurement data occurring in coagulation analysis in different situations. FIG. 5a shows an example where the measurement data defines a non-stationary baseline and an (actual) asymptotic line being parallel. In another example as shown in FIG. 5b, a baseline can be (relatively) flat while the asymptotic line is linearly increasing. In still another example depicted in FIG. 6a the baseline is increasing while the asymptotic line decreases. All these different shapes can be modeled with a single global model function in some examples of the present disclosure (e.g., the model function shown in equation 1 above). In this manner, robust and accurate determination of coagulation results can be possible in different situations. Thus, in theory, the same model function could be employed on data originating from many different automated analyzers, assays and environments.

In some examples, a model function can be selected based on information regarding an analyzer generating the measurement data. For example, the information regarding an analyzer includes one or more of information regarding a type of the analyzer, information regarding an assay performed by the analyzer and information regarding reagents used by the analyzer.

For instance, it may be the case that a baseline of a predetermined analyzer is flat in a predetermined setup. In addition, or alternatively, a (virtual or actual) asymptotic line of a predetermined analyzer can be flat. In still other examples, a baseline and a (virtual or actual) asymptotic line can be parallel in some situations. If this type of information is available, an appropriate model function can be selected for the respective circumstances. For example, if the baseline is flat for measurements of a particular analyzer, it is not required that the model function has the capability of modeling a non-stationary baseline. Likewise, if the asymptotic line is flat for measurements of a particular analyzer, it is not required that the model function has the capability of modeling a non-stationary asymptotic line. Dropping these capabilities can further simplify the model function (e.g., reduce a number of fitting parameters) in some examples. This can in turn make the fitting process faster and more robust.

In the example of a model function according to equation 1 or equation 2 above, different simplifications can be made to take into account additional knowledge regarding characteristics of the time series.

For example, dropping the parameter $p_2$ (or setting the parameter $p_2$ to zero) can result in a flat baseline. In the same manner, dropping the parameter $p_4$ (or setting the parameter $p_4$ to zero) can result an asymptotic line which is parallel to the baseline. Accordingly, dropping both the parameters $p_2$ and $p_4$ (or setting the parameters $p_2$ and $p_4$ to zero) can result in a flat baseline and a flat asymptotic line.

These simplifications can be considered when setting up the fitting algorithm or used as an additional condition in the fitting process.

In some examples, a selection of a model function happens during set-up of the analyzer and the selected model function is used unchanged during operation of the analyzer. The model function can be selected for an automated analyzer during factory setup or in a later stage.

Figure 6B:
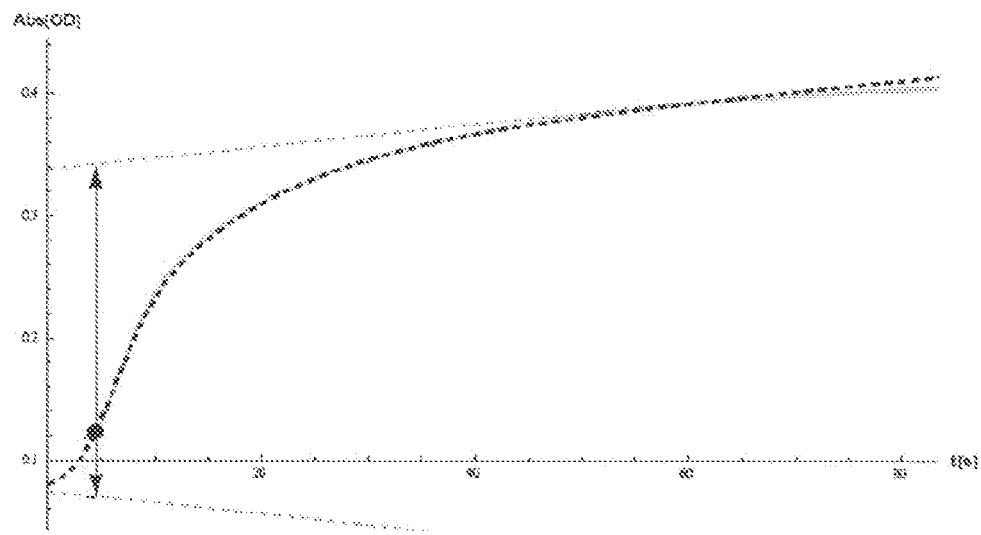

As can be seen in FIG. 6b, the fitting process of the present disclosure can result in valid fits even if a baseline of the time series is missing (e.g., a measurement period has started after a coagulation reaction has started to influence the measurement data). This can be a further advantage of using a global model function over some prior art techniques using multiple model functions for fitting the data.

Validity Checks

In the subsequent section, multiple additional validation steps 54-57 that can be carried out after fitting the global model function to the time series of measurement data will be discussed in connection with FIG. 1. In general, the techniques of the present disclosure can include none, one, or multiple of these validation steps. The one or more validation steps 54-57 (also referred to as 'discrimination steps' herein) allow to distinguish between different classes of fitted model functions (and/or between different classes of time series time series). In particular, a first set of classes can include a "valid" class and an "invalid" class. Fitted model functions in the "valid" class are candidates for further processing. If a fitted model functions is placed in the "invalid" class, this can mean that the underlying time series has major flaws. In addition, or alternatively, a set of classes can include a "negative" class (no clotting reaction has taken place) and a "positive" class (a clotting reaction has taken place and a coagulation result can be determined).

The one or more validation or discrimination steps can use the fitted model function and/or the time series of measurement data for the respective validation processes.

For instance, a validation step can include determining a fitting quality parameter of the fitted model function 54. The quality parameter can be any measure for the quality of the fit to the time series of measurement data. For instance, the fitting quality parameter can be determined based on a deviation of the fitted model function from the time series (e.g., an absolute error of the fitted model function, a standard error of the fitted model function or a higher order module). The fitted curve can be determined to be invalid 55 if the fitting quality parameter is below (or above) a predetermined threshold.

In some examples, the fitting quality parameter is determined using the complete time series of measurement data. In other examples, the fitting quality parameter is determined based on a sub-set of the time series (e.g., a determined clotting time plus a predefined period of time or a predetermined period of time around a clotting time).

In still other examples, determining a fitting quality parameter can include determining if the fitted model function and the time series have a predetermined relationship. For instance, it can be determined if a difference between the fitted model function continuously has a fixed sign, or has a fixed sign over a predetermined sub-section of the time series. If this is the case, the fitted model function can be declared invalid.

In this manner, time series of measurement data which substantially deviate from an expected time series can be detected by the fact that the global model function cannot be fitted closely to the time series. This can indicate that the time series considerably deviates from an expected time series which might mean that the time series does not include proper measurement data.

In addition, or alternatively, a discrimination step between a valid and an invalid fitted model function can include determining one or more features of the fitted model function fulfill one or more predetermined conditions. The one or more features of the fitted model function can include one or more of a maximal slope of the fitted curve, a magnitude of a signal change (e.g., a difference between a baseline and an asymptotic line) and a determined clotting time. The one or more predetermined conditions can include maximum and/or minimum values for the respective features. In addition, or alternatively, the one or more predetermined conditions can include requiring that the respective feature lies within one or more predetermined ranges. For instance, a range of valid clotting times can be defined. In another example, a minimum value of a magnitude of a signal change (e.g., a signal growth or a signal drop) can be set.

In further examples (and possibly in addition to the validation steps discussed above), a discrimination step can include comparing a shape of the fitted model function to one or more expected curve shapes 56 and determining that the fitted model function is valid 57 if the fitted model function resembles the one or more expected curve shapes.

In addition, or alternatively, a discrimination step can include comparing a shape of the fitted model function to one or more erroneous curve shapes and classifying the fitted model function/the time series according to the comparison result. For example, if the fitted model function resembles an erroneous curve shape the fitted model function/time series can be classified in a "negative" class (no clotting reaction has taken place). If the fitted model function does not resemble the erroneous curve shape the fitted model function/time series can be classified in a "positive" class (a clotting reaction has taken place and a coagulation result can be determined).

For example, an erroneous curve shape can be a linear function. If the fitted model function shows a substantially linear behavior (i.e., it has no sigmoidal shape) or resembles a linear function, this can indicate that no clotting reaction to be observed has taken place (i.e., the time series consists of a linear baseline which might be non-flat due to other processes than a clotting reaction to be observed). It can be pointed out that in some examples erroneous curve shapes can be fitted with relatively high quality using the global model functions described in the present disclosure. For instance, the first two terms of equation 1 stated above describe a linear function. Thus, checking only a fitting quality parameter might not be sufficient to decide that a coagulation result can be determined based on the fitted model function in some situations.

Determining if the fitted model function resembles one or more expected or erroneous curve shapes can include performing an F-test or other statistical test to check a hypothesis that the fitted model function resembles the one or more expected or erroneous curve shapes. In one example, the fitted model function can be compared to a linear model of the time series. If the fitted model function resembles the linear model (e.g., as determined by an F-test), the fitted model function can be classified accordingly.

The result of the validity and discrimination checks discussed above can be used in different ways.

In some examples, a coagulation result is only determined if the fitted model function is valid and/or "positive" (it has been determined that a clotting reaction has taken place). In addition, or alternatively, the system carrying out the validity checks can output one or more messages or reports indicating a result of the validity check(s) to a user. For instance, a message can indicate that a fitting quality parameter indicates a bad fit, that a feature of the fitted model function does not meet a certain criterion, or that a curve shape of the fitted model function does not resemble an expected curve shape (e.g., that no clotting reaction has taken place). In one example, the message indicates one or more of a clotting time that is below a predetermined threshold, a clotting time that is above a predetermined threshold, a magnitude of a signal change being below a predetermined threshold or a magnitude of a signal change being above a predetermined threshold.

In other examples, an automated analyzer can perform one or more operations depending on the outcome of the validity checks. For instance, the automated analyzer can order one or more validation operation of the sample having yielded the erroneous result, a repetition of the fitting operations and/or a repetition of the coagulation analysis on a new sample.

The validity checks and the remaining steps of the techniques described herein can be performed in any order (with the proviso that steps required to carry out further steps are carried out first). For example, even though FIG. 1 shows a particular sequence of a first and second validity check, the sequence of these checks can also be reversed. In addition, one or more validity checks might happen after determination of the coagulation result.

The validation checks discussed above can allow for a relatively simple and reliable determination if a fitted model function is a good fit of the times series of measurement data and/or if the time series describe a valid measurement.

Signal Jump Correction

In one additional step that can be combined with any of the techniques of the present disclosure, the methods can further comprise determining that the time series representing measurement data includes one or more signal jumps based on the fitted model function and correcting the one or more signal jumps.

Signal jumps can be artifacts that can be caused by (relatively sudden) changes in a measurement apparatus generating the time series of measurement data. For example, a sample vessel or a detection unit can move during measurement which can result in a signal jump. Other causes for a signal jump are air bubbles moving though the sample a passing a window of the measurement apparatus.

Regardless of the cause of the signal jump, determining that the time series representing measurement data includes one or more signal jumps based on the fitted model function can include searching values of the time series for which a plurality of neighboring earlier data values lie below the fitted model function and a plurality of neighboring later data values lie above the fitted model function, or vice versa. For example, the technique can include searching for data values for which a difference between three or more (or ten or more) data values of the fitted model function and the time series of measurement data on either side of the data values have opposing signs. In a further step, the so detected signal jumps can be corrected (e.g., by shifting data points on either side of the signal jump).

The techniques of the present disclosure can allow for a relatively simple signal jump detection in some examples. As a global model function is employed, a signal jump can cause a characteristic signature which can be detected relatively easily in some examples.

Further Embodiments

The preceding detailed description provides multiple example methods for determining a coagulation result of a biological sample and systems for determining a coagulation result of a biological sample. However, the methods for determining a coagulation result of a biological sample and systems for determining a coagulation result of a biological sample can also be implemented as one of the methods or systems as set out in the following:

An automated method for determining a coagulation result of a biological sample is presented. The method can comprise obtaining a time series representing measurement data of a biological sample. The time series can span a period in which a clotting reaction is supposed to take place in the biological sample. The method can further comprise obtaining a global model function configured to model measurement data of a biological sample in which a clotting reaction takes place. The global model function can be configured to model the measurement data as a sigmoidal shape with at least one inflection point. The absolute value of the maximum curvature of the sigmoidal shape can be larger on one side of the at least one inflection point than on the other side. The method can further comprise fitting the model function to the time series representing measurement data to obtain a fitted global model function and determining a coagulation result of the biological sample based on the fitted global model function.

The global model function can be configured to model a non-flat baseline on a first side of the sigmoidal shape and/or a non-flat virtual or actual asymptotic line of the sigmoidal shape on a second side of the sigmoidal shape.

Determining a coagulation result can include determining a baseline of the sigmoidal shape based on the fitted global model function and determining a virtual or actual asymptotic line based on the fitted global model function. At least one of the baseline and the virtual or actual asymptotic line is non-flat. It can further comprise defining a threshold line running between the baseline and the virtual or actual asymptotic line. A distance between the baseline and the threshold line can be a fixed fraction of a distance between the baseline and the virtual or actual asymptotic line at each point in time. It can further comprise determining the coagulation result based on a feature of the fitted model function at a point where the fitted global model function crosses the threshold line.

The fraction can lie between 0.05 and 0.9.

The coagulation result can be a time when the fitted model function crosses the threshold line or a difference between the baseline and the virtual asymptotic line at the point where the fitted model function crosses the threshold line.

Determining a coagulation result can include determining a baseline of the sigmoidal shape based on the fitted global model function or determining a virtual or actual asymptotic line based on the fitted global model function, defining a threshold line as a fixed multiple of the baseline value or a fixed fraction of the virtual or actual asymptotic line, respectively, at each point in time, and determining the coagulation result based on a feature of the fitted model function at a point where the fitted model function crosses the threshold line.

The baseline or the virtual or actual asymptotic line, or both, can be determined using one or more subset of fitting parameters of the fitted global model function.

The threshold line can be a non-flat linear function.

The baseline can be a linear function.

The baseline and the virtual or actual asymptotic line may not be parallel.

The sigmoidal shape can have a tail with positive or negative curvature.

The global model function can be asymmetric around the inflection point.

The global model function can have different curvature characteristics on both sides of the inflection point.

The coagulation result can be a coagulation time. The coagulation time can be determined as a time of a point of maximum slope of the fitted global model function. The coagulation result can be a magnitude of a signal change determined based on the fitted global model function.

The magnitude of the signal change can be defined as a difference between a baseline and a virtual or actual asymptotic line of the fitted global model function.

The predefined point of time can be a point in time where the fitted model function crosses the threshold line.

The coagulation result can be determined based on a level of the baseline or an extrapolated level of the baseline.

The coagulation result can be determined based on a level of the virtual or actual linear asymptotic line or an extrapolated level of the virtual or actual asymptotic line.

Fitting the model function to the time series can include using a non-linear regression technique. The model function can include a sum of two or more terms. The model function can include a sum of three or four terms. A first term can be a constant term defining a baseline intercept. A second term can be a linear term defining a baseline slope. A third term can be a non-linear term modeling a signal change after a clotting reaction to be monitored has started. The third term can be a product of a linear component and two or more exponential components. The linear component can define a virtual or actual asymptotic line. Each of the two or more exponential components can be a symmetric sigmoid. The exponential components can have the form $1/(1+\exp(-Kn))$, where Kn is a term which increases linearly with time. A fourth term can be a non-linear term defining a non-linear behavior in a tail of the model function. The fourth term can be a sigmoid.

The model function can include more than 5 fitting parameters, optionally less than 15 fitting parameters. A first fitting parameter can define a baseline intercept. A second fitting parameter and the first fitting parameter can define a baseline slope. A third fitting parameter can influence a difference of an intercept of a virtual or actual asymptotic line to an intercept of the base line. A fourth fitting parameter can influence a slope of a virtual or actual asymptotic line. A fifth fitting parameter can define a steepness of a first sigmoid defining a non-linear portion of the sigmoidal shape which can model an influence of a clotting reaction to be observed. A sixth fitting parameter can define a position in time of an inflection point of a first sigmoid defining a non-linear portion of the sigmoidal shape which can model an influence of a clotting reaction to be observed. A seventh fitting parameter can define a steepness of a second sigmoid defining a non-linear portion of the sigmoidal shape which can model an influence of a clotting reaction to be observed. An eighth fitting parameter can define a position in time of an inflection point of a second sigmoid defining a non-linear portion of the sigmoidal shape which can model an influence of a clotting reaction to be observed. A ninth fitting parameter can define an amplitude of a non-linear change of a tail in the measurement data. A tenth fitting parameter can model a curvature of a tail of the measurement data.

The model function can have the form:

$$f_m(x, \vec{p}) = p_1\left(1 + p_2 \cdot x + \frac{p_3(1 + p_4 \cdot x)}{(1 + e^{-p_5(x-p_6)}) \cdot (1 + e^{-p_7(x-p_8)})}\right),$$

or a mathematically equivalent formulation, wherein $p_i$ are fitting parameters and x denotes a time value of the time series to be fitted.

The model function can have the form:

$$f_m(x, \vec{p}) = p_1\left(1 + p_2 \cdot x + \frac{p_3(1 + p_4 \cdot x)}{(1 + e^{-p_5(x-p_6)}) \cdot (1 + e^{-p_7(x-p_8)})} + \frac{p_9}{(1 + e^{-p_{10}(x-x_{max})})}\right),$$

or a mathematically equivalent formulation, wherein $p_i$ are fitting parameters, wherein x denotes a time value of the time series to be fitted and wherein $x_{max}$ is another fitting parameter or a fixed value.

The measurement data can be obtained by an optical or electrical measurement, optionally a turbidity measurement, an absorbance measurement, a scattering measurement or an impedance measurement.

The automated method can further comprise obtaining information regarding an analyzer generating the measurement data and selecting the model function to be used in the fitting step. The information regarding an analyzer can include one or more of information regarding a type of the analyzer, information regarding an assay performed by the analyzer, and information regarding reagents used by the analyzer. Selecting the model function can happen during set-up of the analyzer. The selected model function can be used unchanged during operation of the analyzer.

Fitting the model function to the time series of data can comprise using one or more predefined conditions. The one or more predefined conditions can be defined during set-up of the analyzer. The one or more predefined conditions can be used unchanged during operation of the analyzer. The predefined conditions can include one or more of: a condition that a baseline is flat, a condition that a virtual or actual asymptotic line is flat and a condition that a baseline and a virtual or actual asymptotic line are parallel.

Clotting reaction can be triggered by adding a substance to the biological sample. The substance can be a reagent.

The method can further include one or more discrimination steps to distinguish between different classes of measurement data. The discrimination steps can include determining a fitting quality parameter of the fitted model function, optionally wherein the fitting quality parameter is determined based on a standard error of the fitted model function, and determining a validity of the fitted global model function based on the fitting quality parameter. Fitted model function can be determined to be invalid if the fitting quality parameter is below or above a predetermined threshold. The discrimination steps can include determining one or more features of the fitted model function and determining if the one or more features fulfill one or more predetermined conditions. The one or more features of the fitted model function can include one or more of: a maximal slope of the fitted mode function, a signal difference between a baseline and a virtual asymptotic line and a clotting time. The discrimination step can include comparing a shape of the fitted model function with one or more expected curve shapes and determining that the fitted model function is valid if the fitted model function resembles the one or more expected curve shapes. The discrimination step can include comparing a shape of the fitted model function with one or more negative curve shapes and only determining the coagulation result of the biological sample if the fitted global model function does not resemble the one or more negative curve shapes. The discrimination step can includes comparing the fitted model function to a linear function and determining that no clotting reaction has taken place if the fitted model function resembles the linear function.

The automated method can further comprise determining that the time series representing measurement data includes one or more signal jumps based on the fitted model function and correcting the one or more signal jumps. Determining that the time series representing measurement data includes one or more signal jumps based on the fitted model function can include searching values of the time series for which a plurality of neighboring earlier data values lie below the fitted model function and a plurality of neighboring later data values lie above the fitted model function, or vice versa.

The time series can span a period starting before a clotting reaction is supposed to start and ending when a clotting reaction is supposed to have saturated.

A system for determining a coagulation result of a biological sample is presented. The system can be configured to obtain a time series representing measurement data of a biological sample, wherein the time series spans a period in which a clotting reaction is supposed to take place in the biological sample, obtain a global model function configured to model measurement data of a biological sample in which a clotting reaction takes place, wherein the global model function is configured to model the measurement data as a sigmoidal shape with at least one inflection point and wherein the absolute value of the maximum curvature of the sigmoidal shape is larger on one side of the at least one inflection point than on the other side, fit the model function to the time series representing measurement data to obtain a fitted global model function, and determine a coagulation result of the biological sample based on the fitted global model function.

The system can further comprise an automated analyzer configured to generate measurement data of a biological sample.

The system can be further configured to perform the any of the above methods.

A computer-readable medium having stored instructions thereon which when carried out on a processing system make the processing system carry out the steps of any of the above methods.

Computer-Implementation

Further disclosed and proposed is a computer program including computer-executable instructions for performing the method in one or more of the embodiments enclosed herein when the program is executed on a computer or computer network. Specifically, the computer program may be stored on a computer-readable data carrier. Thus, specifically, one, more than one or even all of method steps as disclosed herein may be performed by using a computer or a computer network, preferably by using a computer program.

Further disclosed and proposed is a computer program product having program code, in order to perform the method in one or more of the embodiments enclosed herein when the program is executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed is a modulated data signal which can contain instructions readable by a computer system or computer network, for performing the method according to one or more of the embodiments disclosed herein.

Referring to the computer-implemented embodiments, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing measurements.

Further disclosed and proposed is a computer or computer network comprising at least one processor, wherein the processor can be configured to perform the method according to one of the embodiments described in this description.

Further disclosed and proposed is a computer loadable data structure that can be configured to perform the method according to one of the embodiments described in this description while the data structure is being executed on a computer.

Further disclosed and proposed is a storage medium, wherein a data structure can be stored on the storage medium and wherein the data structure can be configured to perform the method according to one of the embodiments described in this description after having been loaded into a main and/or working storage of a computer or of a computer network.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. An automated method for determining a coagulation result of a biological sample, the method comprising:
    obtaining a time series representing measurement data of a biological sample, wherein the time series spans a period in which a clotting reaction is supposed to take place in the biological sample;
    obtaining a global model function configured to model measurement data of a biological sample in which a clotting reaction takes place, wherein the global model function is configured to model the measurement data as a sigmoidal shape with at least one inflection point and wherein the absolute value of the maximum curvature of the sigmoidal shape is larger on one side of the at least one inflection point than on the other side;
    fitting the model function to the time series representing measurement data to obtain a fitted global model function; and
    determining a coagulation result of the biological sample based on the fitted global model function,
    wherein determining a coagulation result comprises:
        determining a baseline of the sigmoidal shape based on the fitted global model function,
        determining a virtual or actual asymptotic line based on the fitted global model function, wherein a virtual asymptotic line is an asymptotic line that the fitted model function would approach in the absence of interfering processes and wherein at least one of the baseline and the virtual or actual asymptotic line is non-flat,
        defining a threshold line running between the baseline and the asymptotic line, wherein a distance between the baseline and the threshold line is a fixed fraction of a distance between the baseline and the virtual or actual asymptotic line at each point in time, and
        determining the coagulation result based on a feature of the fitted global model function at a point where the fitted global model function crosses the threshold line.

2. The automated method of claim 1, wherein the global model function is configured to model a non-flat baseline on a first side of the sigmoidal shape and/or a non-flat asymptotic line which the sigmoidal shape approaches on a second side of the sigmoidal shape.

3. The automated method of claim 2, wherein the sigmoidal shape has a tail with positive or negative curvature which means that the fitted model function does not approach a linear asymptotic function.

4. The automated method of claim 1, wherein the baseline or the virtual or actual asymptotic line, or both, are determined using one or more subset of fitting parameters of the fitted global model function.

5. The automated method of claim 1, wherein the coagulation result is a magnitude of a signal change or a coagulation time determined based on the fitted global model function.

6. The automated method of claim 1, wherein the global model function includes a sum of three or four terms, wherein a first term is a constant term defining a baseline intercept, wherein a second term is a linear term defining a baseline slope and wherein the third term is a product of an additional linear component and two or more exponential components defining a non-linear behavior of the sigmoidal shape.

7. The automated method of claim 1, wherein the global model function has the form:

$$f_m(x, \vec{p}) = p_1\left(1 + p_2 \cdot x + \frac{p_3(1 + p_4 \cdot x)}{(1 + e^{-p_5(x-p_6)}) \cdot (1 + e^{-p_7(x-p_8)})}\right),$$

or a mathematically equivalent formulation, wherein $p_i$ are fitting parameters and x denotes a time value of the time series to be fitted, or wherein the global model function has the form:

$$f_m(x, \vec{p}) = p_1\left(1 + p_2 \cdot x + \frac{p_3(1 + p_4 \cdot x)}{(1 + e^{-p_5(x-p_6)}) \cdot (1 + e^{-p_7(x-p_8)})} + \frac{p_9}{(1 + e^{-p_{10}(x-x_{max})})}\right),$$

or a mathematically equivalent formulation, wherein $p_i$ are fitting parameters, wherein x denotes a time value of the time series to be fitted and wherein $x_{max}$ is another fitting parameter or a predefined value.

8. The automated method of claim 1, further comprising,
    obtaining information regarding an analyzer generating the measurement data; and
    selecting the global model function to be used in the fitting step, wherein the information regarding an analyzer includes one or more of information regarding a type of the analyzer, information regarding an assay performed by the analyzer and information regarding reagents used by the analyzer.

9. The automated method of claim 1, wherein determining a coagulation result based on the fitted global model function includes one or more discrimination steps to distinguish between different classes of measurement data.

10. The automated method of claim 9, wherein the discrimination steps include determining a fitting quality parameter of the fitted global model function (54), wherein the fitting quality parameter is a standard error of the measurement data from the fitted global model function, and determining a validity of the fitted global model function based on the fitting quality parameter.

11. The automated method of claim 9, wherein the discrimination steps include comparing a shape of the fitted global model function with one or more negative curve shapes and only determining the coagulation result of the biological sample if the fitted global model function does not resemble the one or more negative curve shapes.

12. The automated method of claim 1, further comprising, determining that the time series representing measurement data includes one or more signal jumps based on the fitted global model function; and
correcting the one or more signal jumps, wherein determining that the time series representing measurement data includes one or more signal jumps based on the fitted global model function includes searching values of the time series for which a plurality of neighboring earlier data values lie below the fitted global model function and a plurality of neighboring later data values lie above the fitted global model function, or vice versa.

13. A computer-readable medium having stored instructions thereon which when carried out on a processing system make the processing system carry out the steps of claim 1.

14. A system for determining a coagulation result of a biological sample, the system configured to:
obtain a time series representing measurement data of a biological sample, wherein the time series spans a period in which a clotting reaction is supposed to take place in the biological sample;
obtain a global model function configured to model measurement data of a biological sample in which a clotting reaction takes place, wherein the global model function is configured to model the measurement data as a sigmoidal shape with at least one inflection point and wherein the absolute value of the maximum curvature of the sigmoidal shape is larger on one side of the at least one inflection point than on the other side;
fit the model function to the time series representing measurement data to obtain a fitted global model function; and
determine a coagulation result of the biological sample based on the fitted global model function, wherein to determine a coagulation result comprises to:
determine a baseline of the sigmoidal shape based on the fitted global model function,
determine a virtual or actual asymptotic line based on the fitted global model function, wherein a virtual asymptotic line is an asymptotic line that the fitted model function would approach in the absence of interfering processes and wherein at least one of the baseline and the virtual or actual asymptotic line is non-flat,
define a threshold line running between the baseline and the asymptotic line, wherein a distance between the baseline and the threshold line is a fixed fraction of a distance between the baseline and the virtual or actual asymptotic line at each point in time, and
determine the coagulation result based on a feature of the fitted global model function at a point where the fitted global model function crosses the threshold line.

* * * * *